United States Patent [19]
Chang et al.

[11] Patent Number: 5,688,249
[45] Date of Patent: Nov. 18, 1997

[54] TELESCOPING MEMBERS FOR CATHETER INTRODUCER ASSEMBLY

[75] Inventors: Joseph Jawshin Chang, Avon; Dennis Bialecki, Oxford; Mark Panzera; Philip D. Schmidt, both of Bristol, all of Conn.

[73] Assignee: Johnson & Johnson Medical, Inc., Arlington, Tex.

[21] Appl. No.: 412,482

[22] Filed: Mar. 28, 1995

[51] Int. Cl.$^6$ ............................................. A61M 5/32
[52] U.S. Cl. .................... 604/198; 604/164; 604/171; 604/192; 604/263
[58] Field of Search .......................... 604/164, 171, 604/198, 263

[56] References Cited

U.S. PATENT DOCUMENTS

| | | | |
|---|---|---|---|
| 4,917,669 | 4/1990 | Bonaldo | 604/164 |
| 4,944,728 | 7/1990 | Carrell et al. | 604/164 |
| 4,950,252 | 8/1990 | Luther et al. | 604/198 |
| 5,000,740 | 3/1991 | Ducharme et al. | 604/162 |
| 5,067,945 | 11/1991 | Ryan et al. | 604/198 |
| 5,098,389 | 3/1992 | Cappucci | 604/164 X |
| 5,102,394 | 4/1992 | Lasaitis et al. | 604/164 |
| 5,135,502 | 8/1992 | Koenig, Jr. et al. | 604/164 |
| 5,135,505 | 8/1992 | Kaufman | 604/263 X |
| 5,215,525 | 6/1993 | Sturman | 604/164 |
| 5,215,528 | 6/1993 | Purdy et al. | 604/164 |
| 5,248,301 | 9/1993 | Koenig, Jr. et al. | 604/164 |
| 5,279,590 | 1/1994 | Sinko et al. | 604/263 |
| 5,388,589 | 2/1995 | Davis | 604/164 X |
| 5,403,283 | 4/1995 | Luther | 604/164 |
| 5,520,654 | 5/1996 | Wahlberg | 604/164 |
| 5,531,713 | 7/1996 | Mastronardi et al. | 604/263 |

Primary Examiner—Sam Rimell
Assistant Examiner—Robert V. Racunas
Attorney, Agent, or Firm—Joseph F. Shirtz

[57] ABSTRACT

The disclosed invention provides a telescoping tip protector for reducing the risk of needle sticks in used catheter introducers. The pair of telescoping members are adapted such that they telescope from a housing which is gripped by the user with one of the telescoping members locking in a position extending from the housing and the second member locks in a position extending from the first member. The second member carries thereon a tip protecting portion which surrounds the cannula tip and prevents the inadvertent jabbing, piercing or sticking of the needle into a person after the use of the introducer and engagement of the protector.

20 Claims, 11 Drawing Sheets

TELESCOPING MEMBERS FOR CATHETER INTRODUCER ASSEMBLY

FIELD OF THE INVENTION

This invention relates to medical devices and in particular to introducers for over the needle catheter assemblies.

BACKGROUND OF THE INVENTION

For the most part there are two types of catheter introducer assemblies for peripheral intravenous catheters. The first type of introducer assembly is a through the needle assembly in which a catheter introducer receives within a sharpened cannula a tubular catheter member. The introducer pierces the skin and the vein and is thereafter drawn up the length of the catheter tube while the catheter tube is inserted into the vein of the patient. The introducer may either be withdrawn into a safe position or split and removed all together from the tubular catheter after emplacement.

The second type of introducer assembly is an over the needle assembly in which the tubular catheter is placed over a sharpened cannula or needle with the sharpened point exposed beyond the end of the tubular catheter. The point then is used to pierce the skin and vein and enter into the vein. Thereafter the tubular catheter is slid off and introduced into the vein and the needle is withdrawn from inside the tubular catheter. During this operation it is necessary for a certain amount of blood to flow up the hollow needle into a flash chamber in order to show the user that proper emplacement has been made.

After removal of the needle from within the catheter several other operations such as taping and attachment of the catheter to a fluid supply take place before final disposition of the introducer assembly. During this time the introducer assembly is a hazard as it has come into contact with body fluids and the pathogens carried by the body fluids. It has therefore become desirable to provide a safety mechanism that covers the pointed tip of a catheter introducer after use.

SUMMARY OF THE INVENTION

A catheter introducer assembly for introduction of a catheter is provided. The introducer has a housing and a sharpened cannula extending from the housing. A needle tip protector is slidable along the cannula and includes a first and second telescoping members. A first telescoping member telescopes within the needle housing or an associated portion of the needle housing to extend outward therefrom. Upon reaching a predetermined position this first member locks into position extending from the housing. The second member telescopes with the first telescoping member and when moved to an extended position locks in a position holding a protection portion over the tip of the needle in order to reduce the incidence of needle sticks after usage. This second member may have a nose which is adapted to conform to the hub of a catheter unit. It also may be provided with a push off tab in order to ease the protective portion forward into a locking position.

Each of the telescoping members may be provided with a pair of locking tabs which engage corresponding slots or openings in a locking manner. Preferably if such locking tabs are used the tabs have undercut sloping ends to increase the locking force of the tabs once engaged with the slots.

An alternate and preferred embodiment uses stamped metal telescoping members to form the attachment and locking mechanism for the safety assembly. The telescoping members are stamped in a substantially box shape longitudinal members set and provided at each end with one portion of a locking mechanism. The needle tip protector is formed separately, for example, by injection molding and is locked to a first telescoping member via a locking tab and opening arrangement. The two telescoping members slide one within the other such that the box shapes are formed of slightly differing dimensions and are provided at their adjacent ends with cooperating locking features. For example, one telescoping member may be formed with a tab and the second telescoping member may be formed with an opening to receive the tab upon positioning of the tab and opening adjacent one another. Finally, the second telescoping member is provided with a cooperating lock which may be in the form of a pair of opposed arms which lock around a post or wedge formed within the housing of the catheter replacement unit.

BRIEF DESCRIPTION OF THE DRAWINGS

The invention will now be described with reference to the attached drawings wherein.

DETAILED DESCRIPTION OF THE PREFERRED EMBODIMENT

Figure 1:
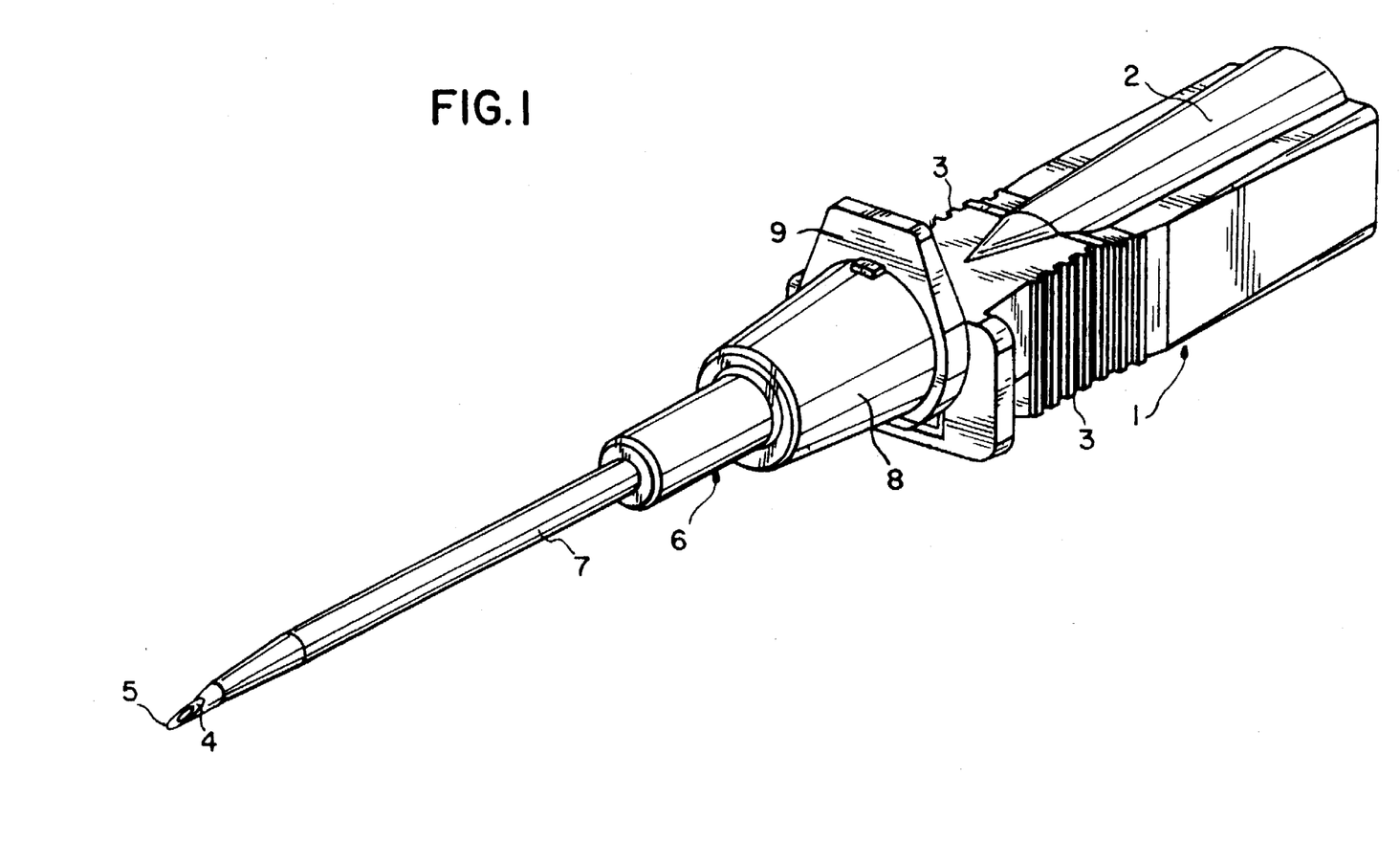
FIG. 1 is a perspective view of an assembly according to the invention having thereon a catheter in place.

Referring to FIG. 1 there is shown a housing 1 having a flash chamber 2 and gripping portion 3. The flash chamber may be formed separately and attached to the housing or may be formed integrally with the housing itself.

The housing 1 has extending therefrom a cannula 4 having a sharpened distal tip 5. Received on the cannula 4 is a tubular catheter 6 having a tubular portion 7 sized for receipt within a vein of a patient. The tubular portion 7 is in fluid communication with a hub 8 which may be formed with a standard luer fitting for attachment of fluid supplies, syringes or the other medical equipment. A push off tab 9 is provided which permits the easy advancement of the tubular catheter 6 along the cannula 4 and off the distal tip 5.

Figure 2:
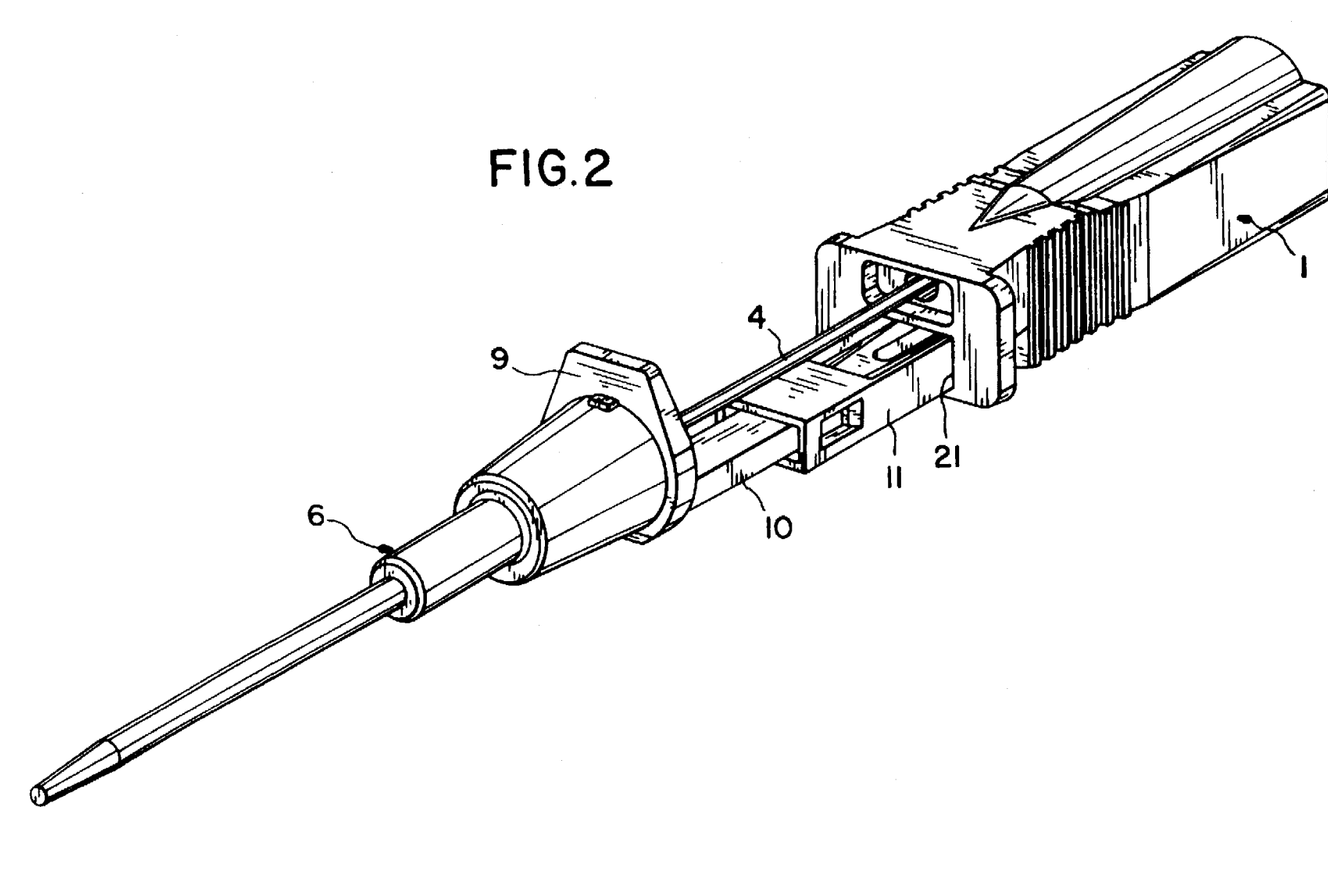
FIG. 2 is a partially extended protective device of the invention.

Referring to FIG. 2 the device is shown in the partially extended condition wherein a telescoping member 10 and telescoping member 11 coact to permit the advancement of the tubular catheter 6 along the cannula 4 while maintaining a degree of attachment of the push off tab and associated protection portion of the device (described below) to the housing 1. In use the cannula is inserted into the vein of the patient and the device is deployed as shown in FIG. 2 by advancing the tubular catheter 6 along the cannula 4.

Figure 3:
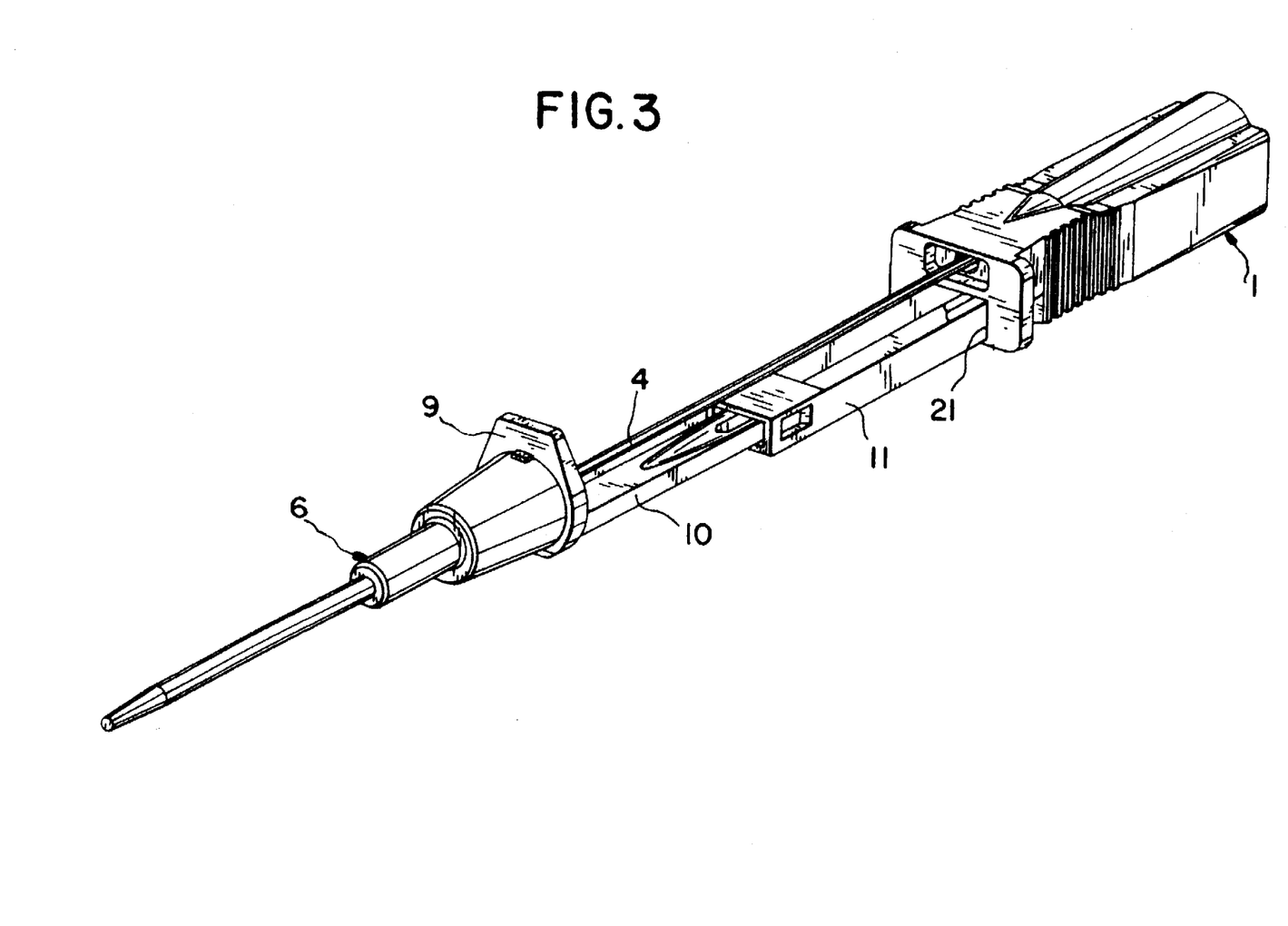
FIG. 3 is a fully extended protective device according to the invention prior to removal of the catheter from the introducer.
Figure 4:
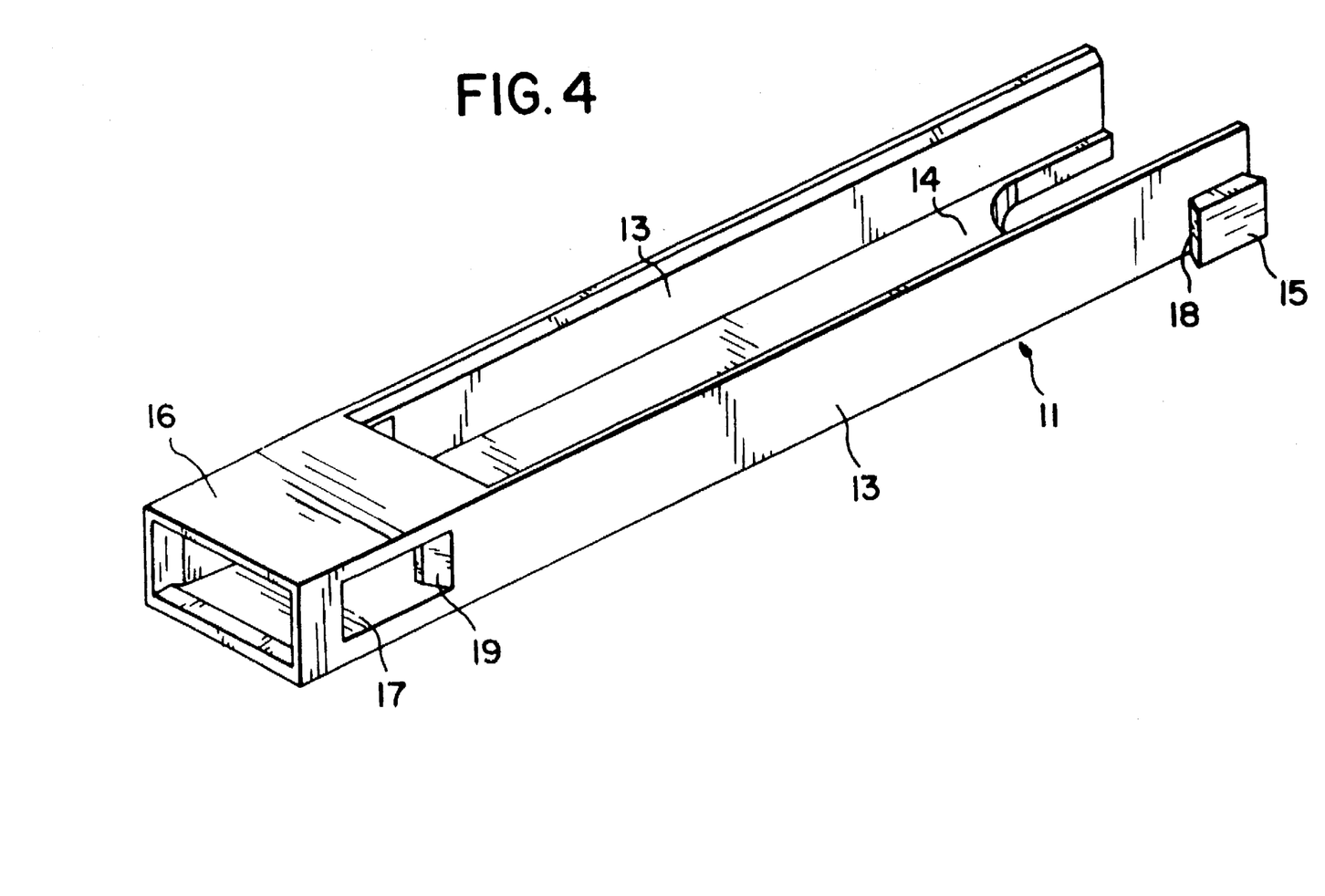
FIG. 4 is a perspective view of one of the members of the locking assembly.

Referring to FIG. 3 the device in the full locked position is shown. The telescoping member 10 and the telescoping member 11 are locked in extended positions holding a protection portion 12 over the distal tip 5 of the cannula (not shown in this Figure). Telescoping member 11 is more clearly shown in FIG. 4. The member has a pair of parallel side walls 13 extending the length thereof and a connecting web 14. Each of the side walls 13 has formed thereon an ear 15 for engagement and locking as will be described below. A box 16 is formed at the opposite end of the telescoping member 11 for receipt and guiding of the telescoping member 10 therein. A pair of openings 17 is defined in the side walls of the box 16 in order to cooperate with ears provided on telescoping member 10 as will be described below. The ears 15 are shown having undercuts 18 which are angled cuts in order to provide an overhang for cooperation with a similar opening provided in the housing 1. The openings provided in the housing 1 may be of any shape that cooperates with ears 15 however, preferably they are formed similarly to the openings 17 at the distal end of the telescoping member 11. As can be seen with reference to the openings formed on telescoping member 11 side walls 13 are angled slightly. Similar walls in the housing opening cooperate with the undercuts 17 to provide a locking function locking the ears 15 within the openings. This description has been in connection with the openings 17 defined in telescoping member 11, however it should be understood that similar openings are formed in the housing and the description is equally as applicable there.

Figure 5:
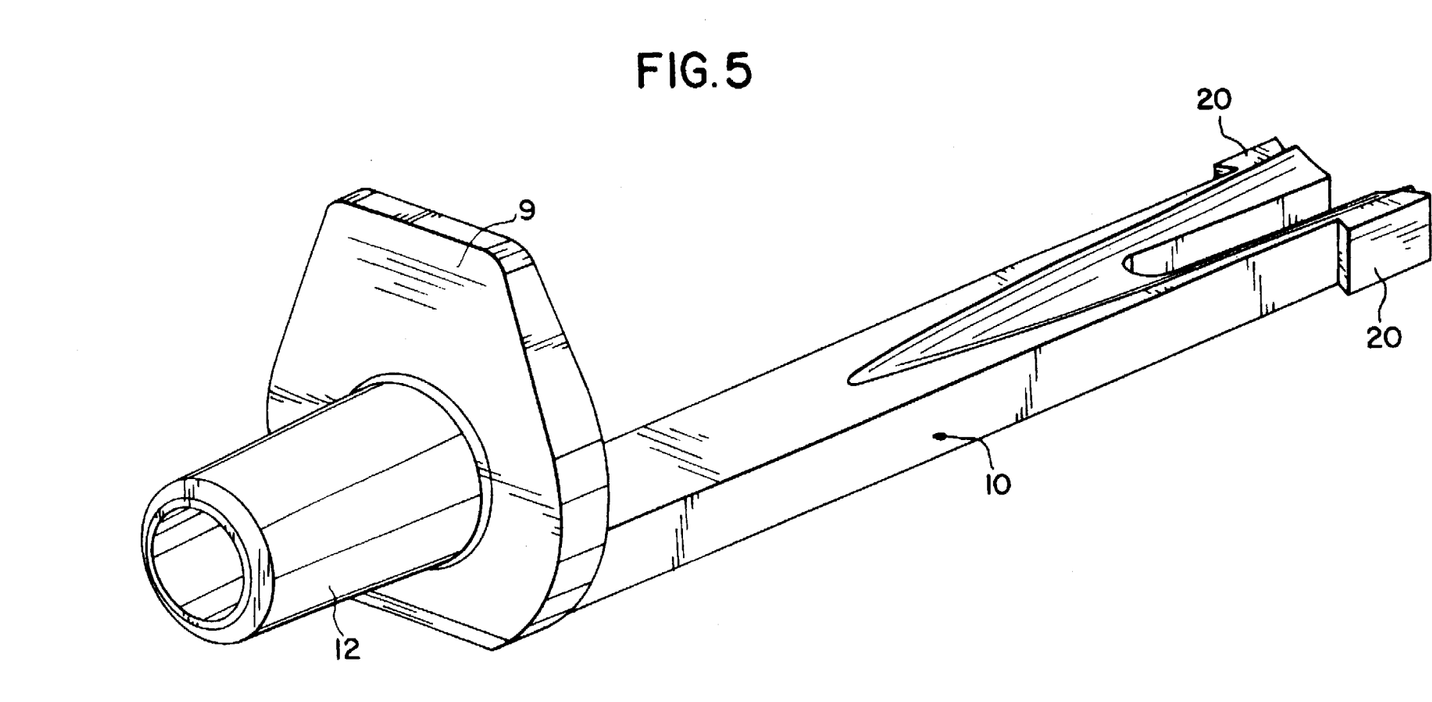
FIG. 5 is a view of a second of the members of the protective portion of the invention.

Referring now to FIG. 5 the telescoping member 10 is shown. This member has a proximal end having ears 19 formed thereon. The ears 20 cooperate with the opening 17 shown in the telescoping member 11 in FIG. 4. The ears 20 are similar in structure and design to those called for in the discussion of telescoping member 11. At the distal end of the telescoping member 10 is a protection portion 12 which is adapted to receive the distal tip 5 of the cannula when the telescoping member 10 and telescoping member 11 are in their fully extended and locked positions. The protection portion 12 has an outer surface which cooperates with the luer fitting of the hub of an appropriate catheter device. A push off tab 9 is formed on the telescoping member 10 in order to provide an area for placement of an operator's thumb or other finger to push the catheter off the cannula. When constructed the telescoping member 10 is received within the box 16 formed by the telescoping member 11. In the unused condition the telescoping member 10 is received within the area between the side walls 13 of telescoping member 11. In use the telescoping member 10 slides distally relative to telescoping member 11 until the ears 20 enter the opening 17 defined in the side walls 13 through operation of a biasing force (i.e., flex of the telescoping member or ear). In a manner similar to that described in connection with telescoping member 11 the ears 20 may be formed in a metal piece by stamping bent tangs which extend outward from the side walls. For cost and other reasons it may be preferred to provide such tangs and a metal piece rather than an injection molded plastic piece as is shown in the figures.

In use the telescoping members are assembled as described above with telescoping member 10 received between the side walls 13 of telescoping member 11. The entire sub assembly of telescoping members 10 and 11 is similarly received slidably within an opening 21 defined by the housing 1. The opening 21 has side walls with similar openings to those provided in telescoping member 11 and referenced as openings 17. The ears 15 of the telescoping member 11 will cooperate with the openings provided within the housing 1 in the side walls of opening 21. In use the cannula is used to pierce the skin and vein of the patient and the catheter is slid off by manual manipulation of protection portion 12 through push off tab 9. Push off tab 9 is moved forward along the cannula which causes telescoping member 10 and telescoping member 11 to slide relative to one another and relative to the housing 1 within opening 21. At the point where telescoping member 11 extends fully from the housing 1 the ears 15 lock within the above-described openings in the side walls of opening 21. At the point wherein telescoping member 10 is fully extending from telescoping member 11 the ears 19 snap into and engage within the openings 17 thus preventing the relative movement of telescoping members 10 and 11. It is thus easily seen that with telescoping member 11 latched or locked relative to the housing 1 and telescoping member 10 latched or locked with respect to telescoping member 11 the protection portion 12 is positioned with the cannula tip received within its internal volume thus protecting the health care workers and patients from accidental sticks.

The device described above is injection molded from plastic in all of its various parts. However, a hybrid piece may be designed in which some of the parts are metal and some of the parts are plastic or a device where substantially all of the parts are metal.

The preferred embodiment, however, is a device wherein the housing and needle tip protector are injection molded from plastic and the telescoping members are formed by stamping metal. This provides the strength and ease of fabrication necessary for mass production. The device will now be described in a hybrid form having a needle protector and housing made of injection molded plastic and telescoping members stamped from metal.

Figure 6:
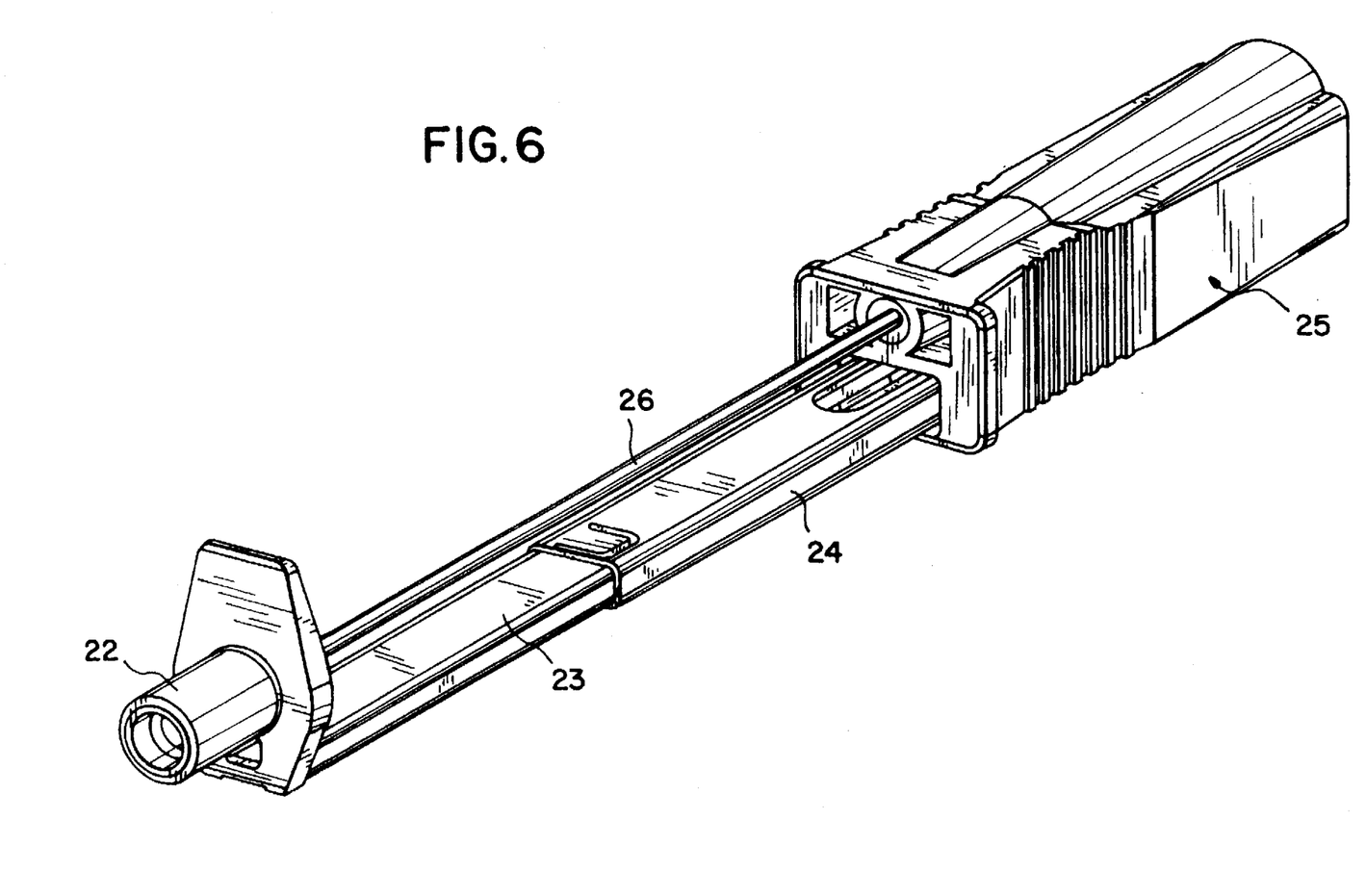
FIG. 6 is a perspective view of a fully extended and locked emplacement unit of the invention having metal telescoping members.

The device is substantially similar to the device described above in that there are provided in operation three pieces which move relative to one another, a telescoping member which is supporting a needle protector that telescopes with a second telescoping members which in turn telescopes within the emplacement housing or holder. FIG. 6 shows a perspective view of the fully extended device made according to the preferred embodiment. There is provided a needle tip protecting portion 22 which is snap-fit in engagement with a stamped metal piece forming the distal telescoping member 23. The distal telescoping member 23 is slidably engaged with (although in the Figure shown is positioned in a locked position) with proximal telescoping member 24. Proximal telescoping member 24 in turn slides within and ultimately locks with housing 25 which is similar to the housing described above in connection with the previous embodiment.

In its locked position as shown in FIG. 6, the needle tip protecting portion is held in a position extending partially beyond the sharpened tip of the cannula 26 such that the sharpened tip is enclosed within the protecting portion.

Figure 7:
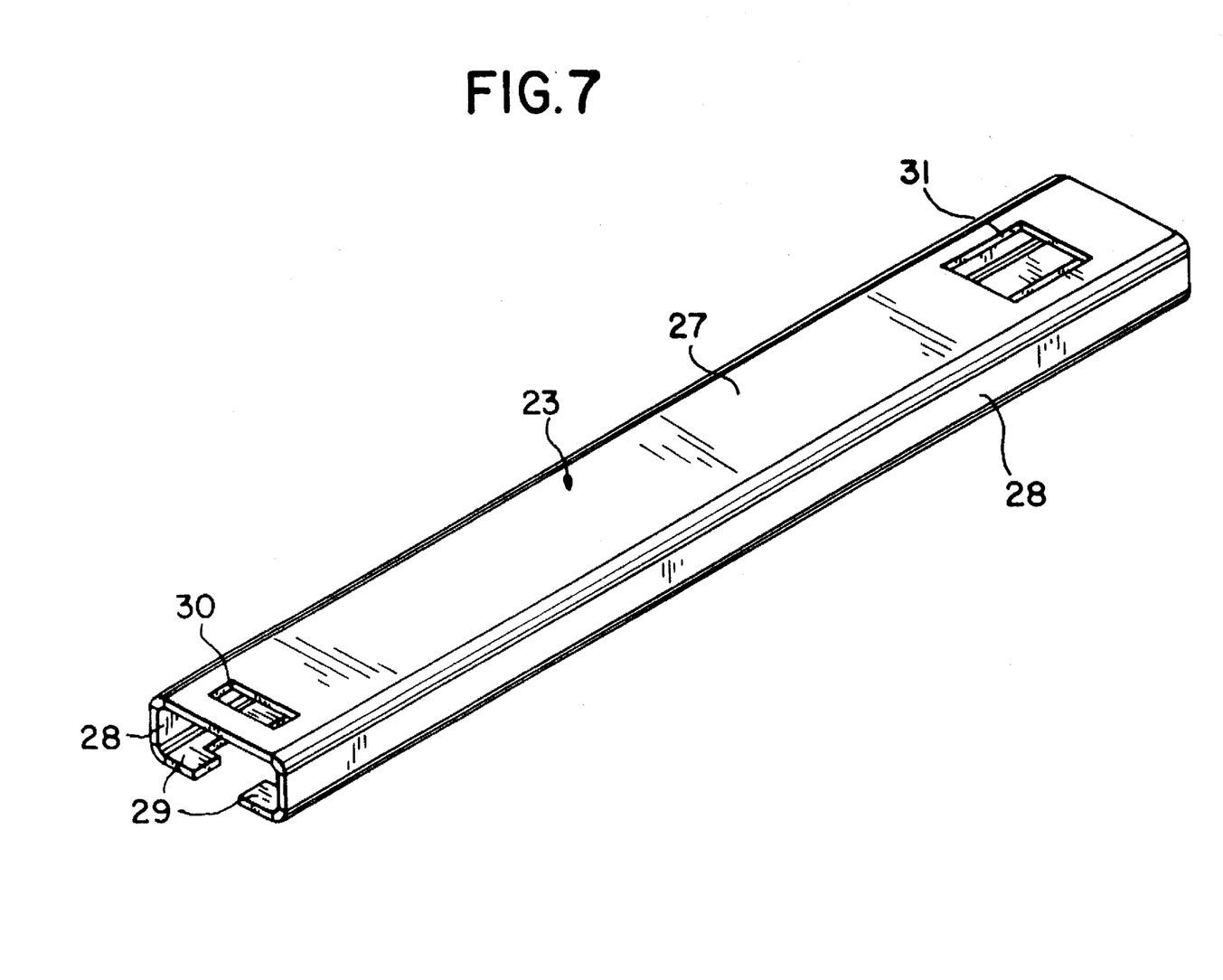
FIG. 7 is a perspective view of the first forward-most telescoping member.

FIG. 7 shows a perspective view of the distal telescoping member 23. The distal telescoping member 23 has a top web 27 and a pair of side walls 28 depending from the top web. In order to add some rigidity to the member as well as the entire assembly, the side walls terminate with arms 29 which extend parallel to the top web 27 in order to form an enclosure.

Top web 27 defines a distal opening 30 for cooperation with the needle tip protecting portion 22 as will be described below. The top web 27 also defines a proximal opening 31 which forms a portion of the locking apparatus for locking the two telescoping members in their extended positions.

Figure 8:
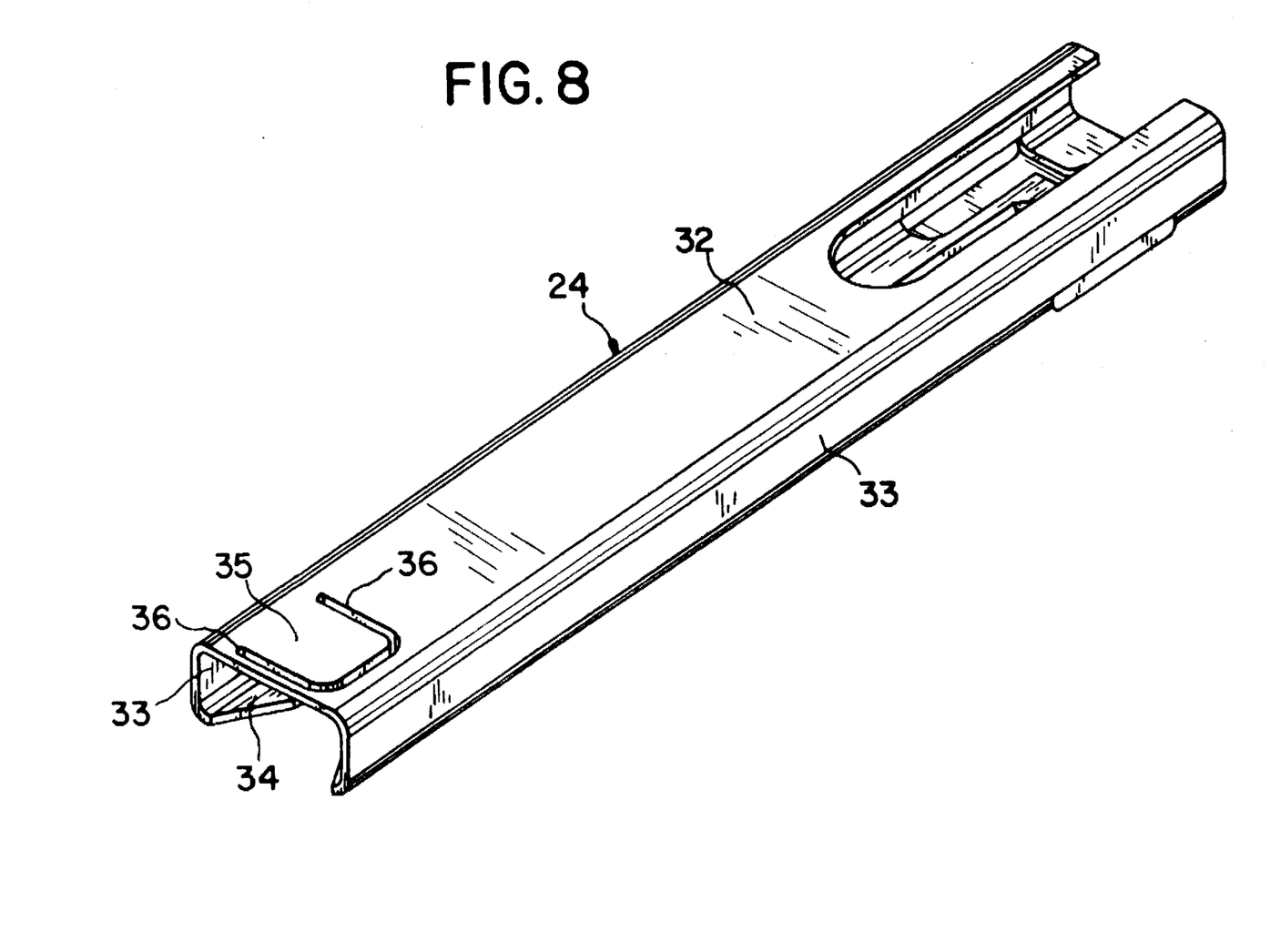
FIG. 8 is a perspective view of the second telescoping member which is proximal to the housing.

FIG. 8 shows the second or proximal telescoping member 24. The proximal telescoping member 24 is formed similarly to the distal telescoping member 23 in that it is stamped from metal and formed with a top web 32 having a pair of depending opposed side walls 33. In a similar fashion, the side walls 33 terminate in arms 34 which extend beneath the top web 32 and in a space but substantially parallel manner to top web 32. However, the arms 34 have a more complex structure and operation in the use of the device as will be described below. A tab 35 is formed in the distal end of the proximal telescoping member. This tab in the device described extends downwardly such that its free end extends below the top web 32. In this way, when the distal telescoping member 23 is received within the proximal telescoping member 24, the tab 35 will ultimately cooperate with the proximal opening 31 in order to lock the two telescoping members together when they are in their appropriate extended position.

As can be seen with reference to FIG. 8, the tab 35 is attached toward one side of the top web 32 and has its free end extending toward the other side. In this way, edges 36 when received within the proximal opening 31 of the distal telescoping member will operate to prevent movement of the telescoping members in either of the longitudinal directions.

Figure 8A:
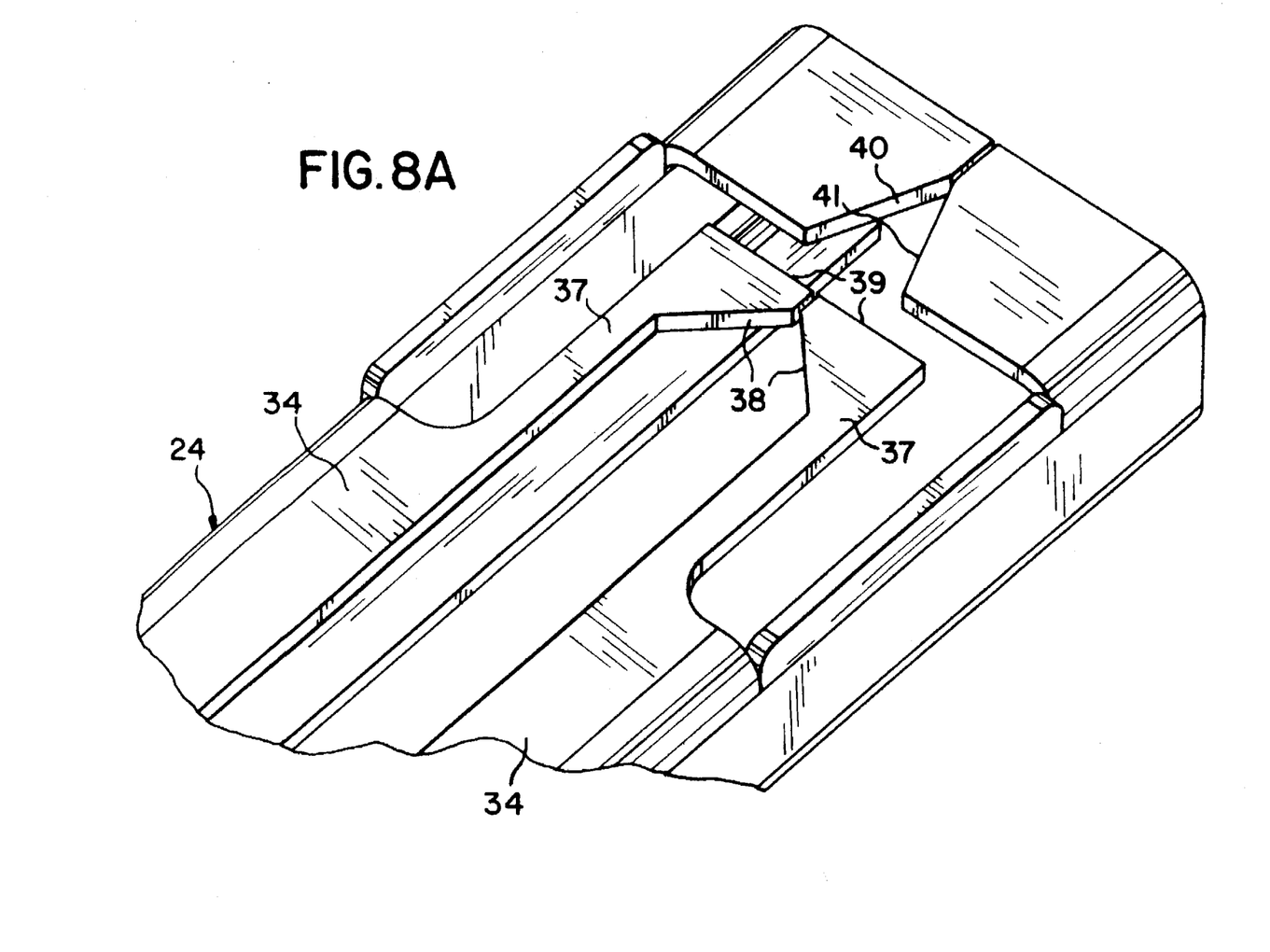
FIG. 8A is perspective view of the proximal end of the telescoping member of FIG. 8.

FIG. 8A is a magnified perspective view of the arms 34 of the proximal telescoping member 24. The view is from the opposite side of FIG. 8 such that the underside of the part can be examined. The arms 34 extend in flexible locking arms 37. The locking arms 37 are formed with a wedging surface 38 on each arm. As will be described below in connection with the housing, a wedge is formed within the housing that rides within the area between the locking arms 37. As the proximal telescoping member 24 is slid to its extended position, the wedge with its narrow end facing the wedging surface 38 ultimately engages the wedging surface 38. The locking arms 37 are sufficiently resilient that the wedge spreads them apart until such time as the wedge passes by locking surface 39 and engages end stop 40. The wedge will then be received within the wedge opening 41 defined in part by the end stop 40 and the locking surface 39.

Although when stamped out of metal, the end stop 40 may be made in the form of two arms as shown in the figure. The piece is encased within an opening in the housing and the arms are sufficiently nonresilient to prevent the wedge from wedging these arms apart and therefore passing the end stop 40. As can be seen with reference to FIG. 8A, the wedge having a triangular shape is received within this wedge opening and held in position. The wedge cannot return beyond the locking arms as the locking surface 39 abuts the flat surface of the wedge and the wedge cannot extend beyond the end stop 40 as the arms are sufficiently nonresilient to prevent the opening and passage of the wedge.

Figure 9:
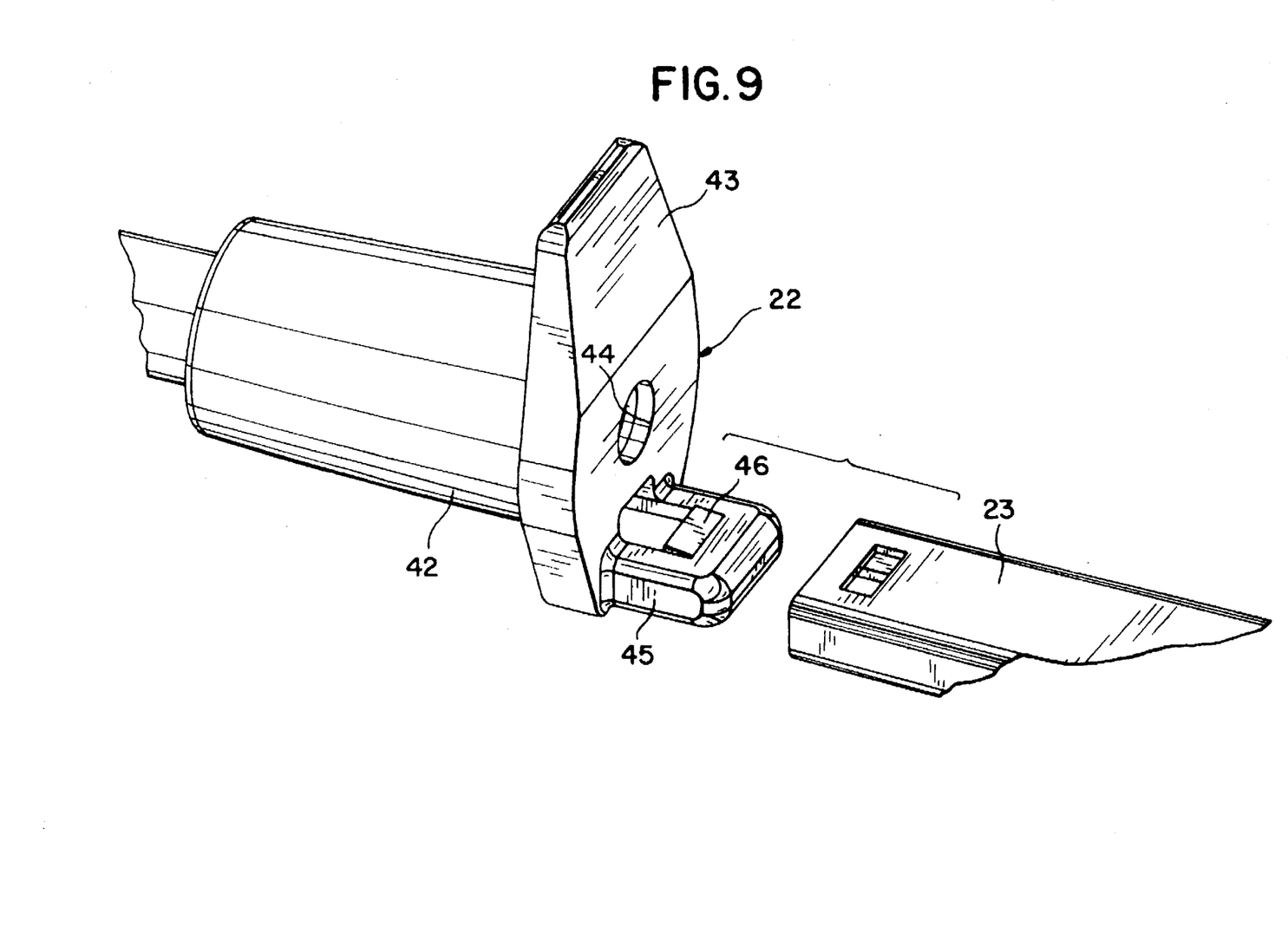
FIG. 9 is a perspective view of the needle protector designed to snap-fit with the telescoping member of FIG. 7; and, FIG. 10 is a perspective view of the emplacement housing.

The needle tip protecting portion 22 will now be described with reference to FIG. 9 wherein the protect end portion 22 is shown having a nose 42 which is similar to the nose described above for receipt within the hub of a catheter. The needle tip protecting portion 22 also provides a finger tab 43 to facilitate pushing forward of the needle tip protecting portion along the cannula until the various telescoping members and housing engaged to lock the needle tip protecting portion 22 in its protecting position. A central opening 44 is defined by the needle tip protecting portion in order to receive the cannula in sliding engagement. A tongue 45 extends rearwardly from the needle tip protecting portion 22 on the side opposite the nose 42. This tongue is sized for receipt within the distal telescoping member 23. The tongue 45 is provided with a tab 46 having a sloped proximal surface and a perpendicular abutment surface on a distal portion. In this way, the distal telescoping member 23 receives the tongue within the space defined by the distal telescoping member and the tab 46 is received within the distal opening 30 to lock the needle tip protecting portion to the distal telescoping member. Once locked in this position with the tongue engaged in the telescoping member, the distal telescoping member and the needle tip protecting portion move as a single unit.

Figure 10:
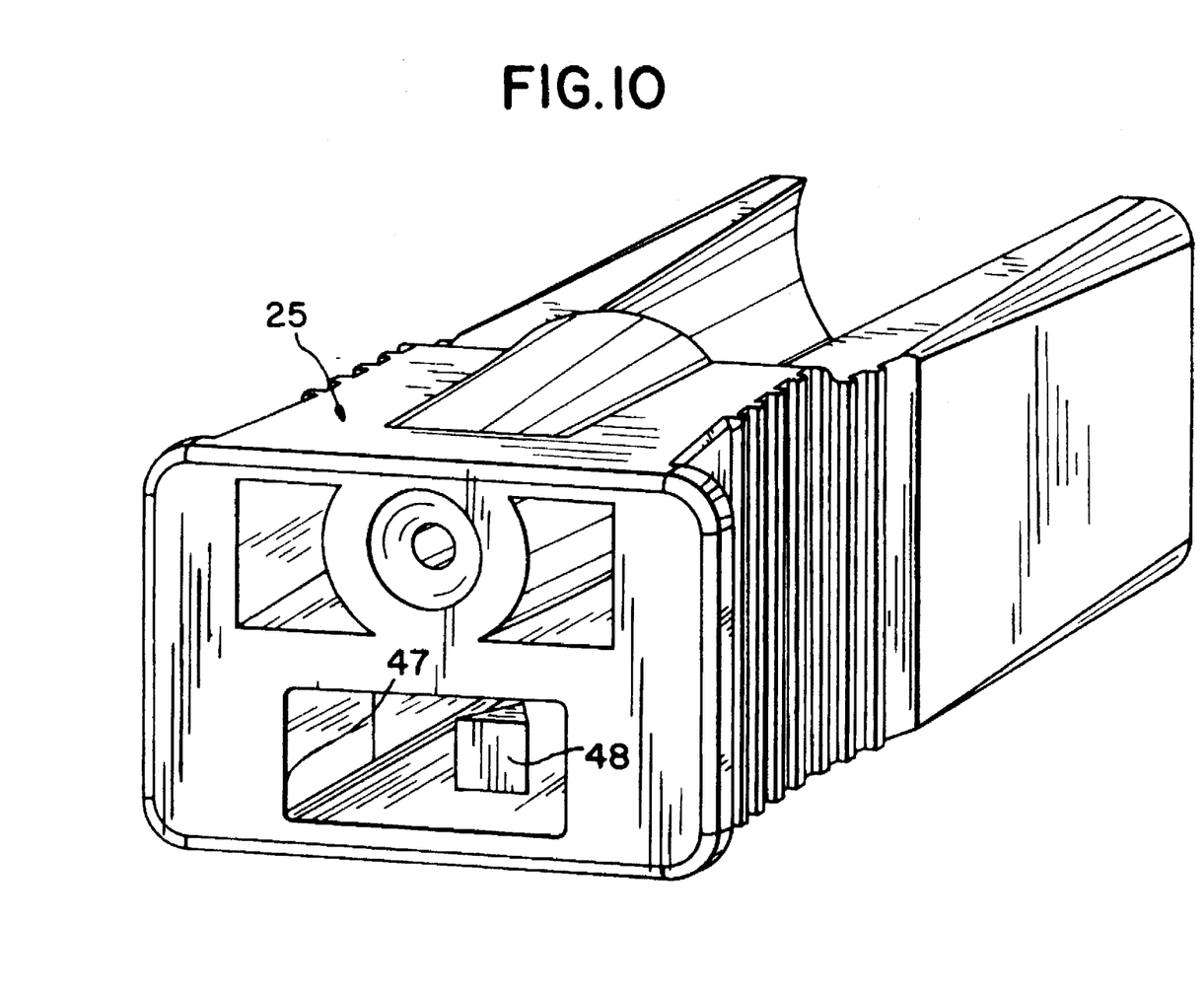

The unique features of the housing 25 will now be described in reference to FIG. 10 which is a perspective view of the housing. As can be seen from this figure, the housing is substantially the same as the housing described above in connection with the all-plastic device. However, the locking mechanism of this housing is slightly different. The housing 25 has a telescope opening 47 for receipt of the telescoping members described above. Prior to locking, the two telescoping members are received within the opening 47 in sliding engagement. The telescope opening 47 has therein a upstanding wedge of substantially triangular cross-sectional shape. The wedge is positioned with its narrow end towards the rear or proximal end of the housing and its flat base presented toward the distal or forward end of the housing. This wedge 48 is the wedge that was described above in connection with the operation of the locking arms 37 and end stop 40. As can be seen when the distal telescoping member is received within the proximal telescoping member 24, the entire unit may then be received within the telescope opening 47. The upstanding wedge slides with the space provided between arms 29 and arms 34 of each of the devices. In use, when the catheter is emplaced within a patient, the needle tip protecting portion is slid forward by finger pressure applied to the pushed finger tab 43. As the needle tip protecting portion 22 is slid distally along the cannula, ultimately, the upstanding wedge 48 engages the wedging surface 38 of the locking arms 37. When sufficient pressure is applied moving the needle tip protecting portion forward, the upstanding wedge 48 pries open the locking arms 37 via its engagement with wedging surface 38 and moves to a position where the arms snap shut behind the wedge and the locking surface 39 engages the distal butt surface of the wedge. In a similar fashion, as the needle tip protecting portion 22 is slid forward, the distal telescoping member 23 and proximal telescoping member 24 slide with respect to one another until such time as the tab 35 is positioned over the proximal opening 31. At this point the tab 35 snaps downwardly into the proximal opening 31 such that the edges 36 engage the outer edges of the proximal 31. As each of these steps takes place the respective telescoping members are prevented from further telescoping in either direction. Once the wedge is appropriately locked with respect to the proximal telescoping member and the proximal and distal telescoping members are locked with respect to one another, then the needle tip protecting portion 22 is held in a predetermine position encasing the sharpened tip of the cannula. Since the various locking mechanisms prevent the telescoping members from sliding with respect to the housing and the telescoping members from sliding with respect to one another, the needle tip protecting portion is held in this position permanently for all practical purposes. That is, although the device may be broken to remove the needle tip protecting portion, there is sufficient strength to prevent the re-exposure of the sharpened tip during normal use and proper disposal of the device.

The device of the present invention has thus been described with respect to its preferred embodiments and certain alternative embodiments. It is easily seen from the discussion that minor variations in material and in configuration of the locks and telescoping members may be made by those of skill in the art without exceeding the scope of the invention and spirit of the claims appended hereto.

We claim:

1. A catheter introducer assembly comprising:
   a) a body;
   b) a cannula having a sharpened tip extending from said body;
   c) a pair of telescoping members received in sliding engagement in an opening defined by a portion of said body;
   d) a tip protector extending from a first of said telescoping members for covering said sharpened tip after introduction of a catheter;
   e) first latch means for latching a second of said telescoping members in a position extending from said body when said second member is moved from a retracted position to a position extending from said body; and,
   f) second latch means for latching said first member in a position extending from said second member when said first member is moved from a first retracted position to a second position extending from said second member; said first latch means comprises at least one resilient arm on one of said body or said second member; and
   g) at least one pawl on said arm and at least one slot positioned opposite said arm such that when said second member moves to said position extending from said body said resilient arm biases said pawl into latched engagement with said slot.

2. The introducer according to claim 1 wherein said second latch means comprises:
   a) at least one resilient arm on one of said first and second members, said arm being biased into an unlatched position prior to latching of said second latch means;
   b) at least one pawl on one of said arm and other of said first and second members; and
   c) at least one slot opposite said pawl and positioned such that when said first member is moved to said position extending from said second member said pawl and said slot are biased into engagement by said resilient arm and said pawl and said slot latch in engagement to hold said first member in said position extending from said second member.

3. The introducer assembly according to claim 1 wherein there are a pair of said arms and a pawl carried by each of said arms and each pawl engages a respective slot upon latching.

4. The introducer assembly according to claim 2 wherein there are a pair of said arms each of said arms having a pawl extending therefrom and at least one slot for engaging said pawls upon latching.

5. The introducer assembly according to claim 1 further comprising a nose formed by said tip protector for engaging a hub on one end of a catheter.

6. The introducer assembly according to claim 1 further comprising a push off tab extending from said tip protector.

7. The introducer assembly according to claim 1 wherein said first and second members have transverse cross-sections that are substantially U-shaped.

8. The introducer assembly according to claim 7 wherein said U-shape is formed of a pair of space sides and an interconnecting web extending between said sides and said sides are positioned and sized to extend from a first side of said cannula to a second side of said cannula to thereby surround said cannula.

9. The introducer assembly according to any one of the claims 2 through 4 wherein at least one pawl is formed having a back cut shaped edge and said slot is defined at least in part by an overhang portion that cooperates with said edge to restrict movement of said pawl out of said slot.

10. The introducer assembly according to claims 1 or 2 wherein said pawl is formed by a metal fin.

11. The introducer assembly according to claims 1 or 2 wherein said first and second members are formed of metal and said pawl is formed by a fin extending from its respective member.

12. The introducer assembly according to claim 11 wherein said slot is an opening defined by the other of said first and second members.

13. The introducer assembly according to claims 1 or 2 wherein at least one pawl is formed of a pair of fins each cooperating with at least one slot to latch against movement in two opposing directions.

14. The introducer assembly according to claim 1 wherein said tip protector is a separate piece from said first of said telescoping members.

15. The introducer assembly according to claim 14 wherein said tip protector is attached to said first of said telescoping members by a snap fit.

16. The introducer assembly according to claim 1 wherein said first latch means comprises at least one resilient arm and a co-operating wedge positioned to engage said resilient arm and bias said resilient arm to a position permitting passage of said wedge in a first direction beyond said resilient arm and return of said resilient arm to a locking position after said wedge moves beyond said resilient arm to engage said wedge and prevent movement of said wedge in a direction opposite said first direction.

17. The introducer assembly according to claim 16 wherein there are two such resilient arms position for movement in different directions.

18. The introducer assembly according to claim 17 wherein said resilient arm at least partially defines a capture opening for receipt of said wedge in a locked position and said capture opening is shaped to prevent further movement of said wedge with respect to said resilient arm.

19. The introducer assembly according to claim 1 wherein said tip protector is formed of molded plastic and said first telescoping member is formed of a metal stamping snap fit to said tip protector.

20. The introducer assembly according to claim 19 wherein said first telescoping member defines a proximal opening and said second telescoping member has a resilient tab attached to said second telescoping member along a base extending in a direction parallel to the telescoping movement of the telescoping members, said tab extending transverse to the direction of said telescoping movement and sized to be received within said proximal opening to prevent telescoping movement of said telescoping members when said telescoping members are moved to said second position.

* * * * *